(12) United States Patent
Ishii et al.

(10) Patent No.: US 7,015,356 B2
(45) Date of Patent: Mar. 21, 2006

(54) PROCESS FOR PRODUCING DICARBOXYLIC ACIDS

(75) Inventors: Yasutaka Ishii, Takatsuki (JP); Yasuteru Kajikawa, Himeji (JP)

(73) Assignee: Daicel Chemical Industries, Ltd., Osaka (JP)

( * ) Notice: Subject to any disclaimer, the term of this patent is extended or adjusted under 35 U.S.C. 154(b) by 3 days.

(21) Appl. No.: 10/450,120

(22) PCT Filed: Dec. 7, 2001

(86) PCT No.: PCT/JP01/10753

§ 371 (c)(1),
(2), (4) Date: Jun. 11, 2003

(87) PCT Pub. No.: WO02/48084

PCT Pub. Date: Jun. 20, 2002

(65) Prior Publication Data

US 2004/0024248 A1 Feb. 5, 2004

(30) Foreign Application Priority Data

Dec. 14, 2000 (JP) ....................... 2000-380450

(51) Int. Cl.
*C07C 51/16* (2006.01)

(52) U.S. Cl. ................ 562/549; 562/542; 562/543; 562/590

(58) Field of Classification Search ........... 562/512, 562/523, 542, 549, 590
See application file for complete search history.

(56) References Cited

U.S. PATENT DOCUMENTS

| | | | | |
|---|---|---|---|---|
| 5,958,821 A | * | 9/1999 | Ishii et al. | 502/167 |
| 5,981,420 A | * | 11/1999 | Nakano et al. | 502/155 |
| 6,642,419 B1 | * | 11/2003 | Miura et al. | 568/357 |
| 2002/0169331 A1 | * | 11/2002 | Miura et al. | 552/1 |
| 2003/0176733 A1 | * | 9/2003 | Kunhle et al. | 562/527 |
| 2004/0014985 A1 | * | 1/2004 | Sugahara | 548/475 |

FOREIGN PATENT DOCUMENTS

| | | |
|---|---|---|
| EP | 824962 A1 | 2/1998 |
| EP | 858835 A1 | 8/1998 |
| JP | 8-038909 | 2/1996 |
| JP | 9-327626 | 12/1997 |
| JP | 10-286467 | 10/1998 |
| JP | 11300212 | * 11/1999 |
| WO | WO 00/48972 A1 | 8/2000 |

OTHER PUBLICATIONS

Ishii et al., Alkane Oxidation with Molecular Oxygen Using a New Efficient Catalytic System: N–Hydroxyphthalimide (NHPI) Combined with Co(acac)n (n=2 or 3), J. Org. Chem., 61 (14), 4520–4526.*

* cited by examiner

*Primary Examiner*—Johann Richter
*Assistant Examiner*—Karl Puttlitz
(74) *Attorney, Agent, or Firm*—Birch, Stewart, Kolasch & Birch

(57) ABSTRACT

A carboxylic acid is produced by oxidative cleavage of a cycloalkane with oxygen and performs a reaction in the presence of a catalyst including an imide compound and a metallic compound, the imide compound having a cyclic imide skeleton represented by the following Formula (I):

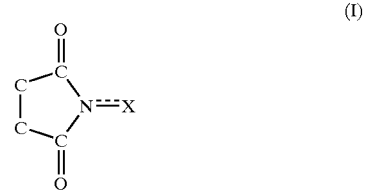

wherein X is an oxygen atom or an —OR group, and wherein R is a hydrogen atom or a hydroxyl-protecting group, under conditions of a reaction temperature of 80° C. or higher and a concentration of the cycloalkane of 21% by weight or more.

14 Claims, No Drawings

PROCESS FOR PRODUCING DICARBOXYLIC ACIDS

This application is the national phase under 35 U.S.C. § 371 of PCT International Application No. PCT/JP01/10753 which has an International filing date of Dec. 7, 2001, which designated the United States of America.

BACKGROUND OF THE INVENTION

1. Field of the Invention

The present invention relates to a process for producing dicarboxylic acids that are useful as, for example, raw materials for polyamides and polyesters, and intermediate materials for fine chemicals. More specifically, it relates to a process of oxidative cleavage of a cycloalkane with oxygen in the presence of a catalyst to thereby yield a corresponding dicarboxylic acid.

2. Description of the Related Art

Certain processes of oxidatively cleaving a cycloalkane and/or a cycloalkanol are known as processes for producing dicarboxylic acids. For example, adipic acid, a raw material for polyamides, is produced by a process of oxidizing cyclohexanol alone or a mixture of cyclohexanol and cyclohexane with nitric acid. However, this process requires expensive facilities for exhaust gas for disposal of nitrogen oxides by-produced in the reaction.

To avoid these problems, certain processes of oxidatively cleaving a cycloalkane with molecular oxygen in the presence of an oxidation catalyst to thereby yield a corresponding dicarboxylic acid have been proposed. For example, Japanese Unexamined Patent Application Publications No. 08-38909, No. 09-327626, and No. 10-286467 each disclose a process of oxidatively cleaving a cycloalkane with oxygen in the presence of a catalyst comprising an imide compound having an N-hydroxy or N-oxo cyclic imide skeleton and a metallic compound to thereby yield a corresponding dicarboxylic acid. However, examples disclosed in these publications use a relatively large amount of the catalyst and do not always achieve sufficiently satisfactory results in their space time yields (STYs). A demand has therefore been made on a process for producing a dicarboxylic acid, which process can reduce the amount of a catalyst, can significantly improve the space time yield and can produce the dicarboxylic acid more efficiently.

SUMMARY OF THE INVENTION

Accordingly, an object of the present invention is to provide a process for producing a corresponding dicarboxylic acid by catalytic oxidation of a cycloalkane with oxygen, which process can yield the dicarboxylic acid in a high space time yield even using a small amount of a catalyst.

To achieve the above object, the present inventors have made intensive and detail investigations on an oxidation reaction of a cycloalkane with oxygen in the presence of a catalyst including an imide compound and a metallic compound. As a result, they have found that a reaction temperature and a concentration of the cycloalkane in a reaction system very significantly affect the space time yield of the resulting dicarboxylic acid. Specifically, they have found that a conversion rate from the cycloalkane is low and the space time yield of the dicarboxylic acid is low when the concentration of the cycloalkane in the reaction system is excessively low or excessively high, and that the conversion rate from the cycloalkane can be significantly improved and the corresponding dicarboxylic acid is produced in a high space time yield even using a reduced amount of the catalyst by setting the reaction temperature at a specific temperature or higher and the concentration of the cycloalkane within a specific range. The present invention has been accomplished based on these findings.

Specifically, the present invention provides a process for producing a dicarboxylic acid by oxidative cleavage of a corresponding cycloalkane with oxygen, wherein a reaction is performed in the presence of a catalyst comprising an imide compound and a metallic compound, the imide compound having a cyclic imide skeleton represented by following Formula (I):

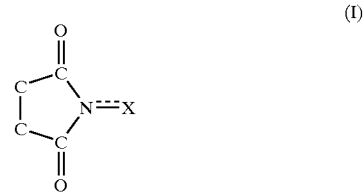

wherein X is an oxygen atom or an —OR group, where R is a hydrogen atom or a hydroxyl-protecting group, under conditions of a reaction temperature of 80° C. or higher and a concentration of the cycloalkane in a system of 21% by weight or more.

The imide compound includes, for example, compounds represented by following Formula (1):

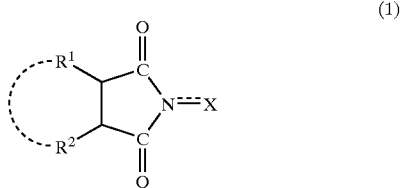

wherein $R^1$ and $R^2$ are the same or different and are each a hydrogen atom, a halogen atom, an alkyl group, an aryl group, a cycloalkyl group, a hydroxyl group, an alkoxy group, a carboxyl group, an alkoxycarbonyl group, or an acyl group, where $R^1$ and $R^2$ may be combined to form a double bond, an aromatic ring, or a non-aromatic ring; X is an oxygen atom or an —OR group, where R is a hydrogen atom or a hydroxyl-protecting group; and wherein one or two of an N-substituted cyclic imido group indicated in the formula may be further formed on the $R^1$, $R^2$, or on the double bond, aromatic ring or non-aromatic ring formed by $R^1$ and $R^2$.

A preferred example of the imide compound is N-hydroxysuccinimide which may have an alkyl group at the α-position and/or the β-position and whose hydroxyl group may be protected by a protecting group.

The amount of the imide compound is, for example, from about 0.000001 to about 0.01 mole per mole of the cycloalkane.

At least one metallic compound selected from compounds of metallic elements belonging to Groups 5, 6, 7, 8, 9, 10, and 11 of the Periodic Table can be used as the metallic compound.

The metallic compound may be a combination of a low-valence metallic compound and a high-valence metallic compound.

The amount of the metallic compound is, for example, from about 0.05 to about 20 moles per mole of the imide compound.

At least one solvent selected from protic organic solvents and nitrites can be used as a reaction solvent.

The material cycloalkane is preferably a compound having a cycloalkane ring containing 5 to 15 members.

DETAILED DESCRIPTION

[Cycloalkanes]

Cycloalkanes (hereinafter briefly referred to as "substrate") are used as a raw material in the present invention.

Such cycloalkanes include, but are not limited to, cyclopropane, cyclobutane, cyclopentane, cyclohexane, cycloheptane, cyclooctane, cyclononane, cyclodecane, cyclododecane, cyclotetradecane, cyclohexadecane, cyclooctadecane, cycloicosane, cyclodocosane, cyclotriacontane, and other cycloalkanes each containing from about 3 to about 30 members. Among them, cyclopentane, cyclohexane, cyclooctane, cyclododecane, and other cycloalkanes each containing about 5 to about 15 members are preferred, of which cyclohexane and cyclododecane are typically preferred.

The cycloalkanes may each have at least one substituent within ranges not adversely affecting the reaction. Such substituents include, but are not limited to, halogen atoms, oxo group, hydroxyl group, mercapto group, substituted oxy groups (e.g., alkoxy groups, aryloxy groups, and acyloxy groups), substituted thio groups, carboxyl groups, substituted oxycarbonyl groups, substituted or unsubstituted carbamoyl groups, cyano group, nitro group, substituted or unsubstituted amino groups, alkyl groups (e.g., methyl, ethyl, isopropyl, t-butyl, hexyl, octyl, decyl, and other $C_1$–$C_{20}$alkyl groups, of which $C_1$–$C_4$ alkyl groups are preferred), alkenyl groups, alkynyl groups, cycloalkyl groups, cycloalkenyl groups, aryl groups (e.g., phenyl and naphthyl groups), aralkyl groups (e.g., benzyl group), and heterocyclic groups. An aromatic or non-aromatic carbon ring or heterocyclic ring may be condensed with the cycloalkane ring of the cycloalkanes within ranges not adversely affecting the reaction. The cycloalkanes can therefore be bridged hydrocarbons.

A corresponding cycloalkanol and/or a cycloalkanone may be added to a reaction system in addition to the cycloalkane. These compounds can be converted into a corresponding dicarboxylic acid.

[Oxygen]

As oxygen, any of molecular oxygen and nascent oxygen can be used. Such molecular oxygen is not specifically limited and includes pure oxygen, oxygen diluted with an inert gas such as nitrogen gas, helium gas, argon gas, and carbon dioxide gas, and air. Oxygen can be generated in the reaction system. The amount of oxygen varies depending on the type of the substrate but is generally 0.5 mole or more (e.g., 1 mole or more), preferably from about 1 to about 100 moles, and more preferably from about 2 to about 50 moles per mole of the substrate. Excess moles of oxygen to the substrate is often used.

[Imide Compound Catalysts]

The imide compound having a cyclic imide skeleton represented by Formula (I) and a metallic compound are used in combination as a catalyst in the present invention.

The bond between the nitrogen atom and X in Formula (I) is a single or double bond. The imide compound may have a plurality of the N-substituted cyclic imide skeleton represented by Formula (I) in its molecule. When X is an —OR group and R is a hydroxyl-protecting group, a plurality of skeletons (N-oxy cyclic imide skeletons) derived from the N-substituted cyclic imide skeleton by removal of R may be combined through R in the imide compound.

The hydroxyl-protecting group represented by R in Formula (I) includes conventional hydroxyl-protecting groups in the field of organic synthesis. Such protecting groups include, but are not limited to, alkyl groups (e.g., methyl, t-butyl, and other $C_1$–$C_4$ alkyl groups), alkenyl groups (e.g., allyl group), cycloalkyl groups (e.g., cyclohexyl group), aryl groups (e.g., 2,4-dinitrophenyl group), aralkyl groups (e.g., benzyl, 2,6-dichlorobenzyl, 3-bromobenzyl, 2-nitrobenzyl, and triphenylmethyl groups); substituted methyl groups (e.g., methoxymethyl, methylthiomethyl, benzyloxymethyl, t-butoxymethyl, 2-methoxyethoxymethyl, 2,2,2-trichloroethoxymethyl, bis(2-chloroethoxy)methyl, and 2-(trimethylsilyl)ethoxymethyl groups), substituted ethyl groups (e.g., 1-ethoxyethyl, 1-methyl-1-methoxyethyl, 1-isopropoxyethyl, and 2,2,2-trichloroethyl groups), tetrahydropyranyl group, tetrahydrofuranyl group, 1-hydroxyalkyl groups (e.g., 1-hydroxyethyl, 1-hydroxyhexyl, 1-hydroxydecyl, 1-hydroxyhexadecyl, 1-hydroxy-1-phenylmethyl groups), and other groups that can form an acetal or hemiacetal group with a hydroxyl group; acyl groups (e.g., formyl, acetyl, propionyl, butyryl, isobutyryl, valeryl, pivaloyl, and other aliphatic $C_1$–$C_6$ acyl groups; acetoacetyl group; benzoyl, naphthoyl, and other aromatic acyl groups), sulfonyl groups (e.g., methanesulfonyl, ethanesulfonyl, trifluoromethanesulfonyl, benzenesulfonyl, p-toluenesulfonyl, and naphthalenesulfonyl groups), alkoxycarbonyl groups (e.g., methoxycarbonyl, ethoxycarbonyl, t-butoxycarbonyl, and other $C_1$–$C_4$ alkoxycarbonyl groups), aralkyloxycarbonyl groups (e.g., benzyloxycarbonyl, and p-methoxybenzyloxycarbonyl groups), substituted or unsubstituted carbamoyl groups (e.g., carbamoyl, methylcarbamoyl, and phenylcarbamoyl groups), groups derived from inorganic acids (e.g., sulfuric acid, nitric acid, phosphoric acid, and boric acid) by removal of OH group, dialkylphosphinothioyl groups (e.g., dimethylphosphinothioyl group), diarylphosphinothioyl groups (e.g., diphenylphosphinothioyl group), and substituted silyl groups (e.g., trimethylsilyl, t-butyldimethylsilyl, tribenzylsilyl, and triphenylsilyl groups).

When X is an -OR group, a plurality of skeletons (N-oxy cyclic imide skeletons) derived from the N-substituted cyclic imide skeleton by removal of R may be combined through R. In this case, examples of R include oxalyl, malonyl, succinyl, glutaryl, phthaloyl, isophthaloyl, terephthaloyl, and other polycarboxylic acyl groups; carbonyl group; methylene, ethylidene, isopropylidene, cyclopentylidene, cyclohexylidene, benzylidene, and other polyvalent hydrocarbon groups, of which groups that can form an acetal bond with two hydroxyl groups are preferred.

Protecting groups other than methyl group and other alkyl groups are more preferred as R. Typically preferred examples of R are hydrogen atom; groups that can form an acetal or hemiacetal group with a hydroxyl group; acyl groups, sulfonyl groups, alkoxycarbonyl groups, carbamoyl groups, and other groups derived from acids (e.g., carboxylic acids, sulfonic acids, carbonic acid, carbamic acid, sulfuric acid, phosphoric acids, and boric acids) by removal of OH group, and other hydrolyzable protecting groups that can be eliminated or deprotected by hydrolysis.

Typical examples of the imide compounds are imide compounds represented by Formula (1). Of the substituents $R^1$ and $R^2$ in the imide compounds, the halogen atom includes iodine, bromine, chlorine and fluorine atoms. The alkyl group includes, but is not limited to, methyl, ethyl, propyl, isopropyl, butyl, isobutyl, s-butyl, t-butyl, hexyl, decyl, and other straight- or branched-chain alkyl groups each containing from about 1 to about 10 carbon atoms. Preferred alkyl groups are alkyl groups each containing from about 1 to about 6 carbon atoms, of which lower alkyl groups each containing from about 1 to about 4 carbon atoms are typically preferred.

The aryl group includes phenyl and naphthyl groups, for example. The cycloalkyl group includes, for example, cyclopentyl and cyclohexyl groups. The alkoxy group includes, for example, methoxy, ethoxy, isopropoxy, butoxy, t-butoxy, hexyloxy, and other alkoxy groups each containing from about 1 to about 10 carbon atoms, and preferably containing from about 1 to about 6 carbon atoms. Among them, lower alkoxy groups each containing from about 1 to about 4 carbon atoms are typically preferred.

Examples of the alkoxycarbonyl group include methoxycarbonyl, ethoxycarbonyl, isopropoxycarbonyl, butoxycarbonyl, t-butoxycarbonyl, hexyloxycarbonyl, and other alkoxycarbonyl groups each containing from about 1 to about 10 carbon atoms in the alkoxy moiety. Preferred carbonyl groups are alkoxycarbonyl groups each containing from about 1 to about 6 carbon atoms in the alkoxy moiety, of which lower alkoxycarbonyl groups each containing from about 1 to about 4 carbon atoms in the alkoxy moiety are typically preferred. The acyl group includes, but is not limited to, formyl, acetyl, propionyl, butyryl, isobutyryl, valeryl, isovaleryl, pivaloyl, and other acyl groups each containing from about 1 to about 6 carbon atoms.

The substituents $R^1$ and $R^2$ may be identical to or different from each other. The substituents $R^1$ and $R^2$ in Formula (1) may be combined to form a double bond, an aromatic ring, or a non-aromatic ring. The preferred aromatic or non-aromatic ring is a 5- to 12-membered ring, and especially a 6- to 10-membered ring. The ring may be a heterocyclic ring or condensed heterocyclic ring, but it is often a hydrocarbon ring. Such rings include, but are not limited to, non-aromatic alicyclic rings (e.g., cyclohexane ring and other cycloalkane rings which may have a substituent, cyclohexene ring and other cycloalkene rings which may have a substituent), non-aromatic bridged rings (e.g., 5-norbornene ring and other bridged hydrocarbon rings which may have a substituent), benzene ring, naphthalene ring, and other aromatic rings (including condensed rings) which may have a substituent. The ring often comprises an aromatic ring. The ring may have at least one substituent. Such substituents include, for example, alkyl groups, haloalkyl groups, hydroxyl group, alkoxy groups, carboxyl group, alkoxycarbonyl groups, acyl groups, nitro group, cyano group, amino groups, and halogen atoms.

On $R^1$, $R^2$, or on the double bond, aromatic ring or non-aromatic ring formed by $R^1$ and $R^2$, one or two of the N-substituted cyclic imido group indicated in Formula (1) may be further formed. For example, when $R^1$ or $R^2$ is an alkyl group containing two or more carbon atoms, the N-substituted cyclic imido group may be formed together with the adjacent two carbon atoms constituting the alkyl group. Likewise, when $R^1$ and $R^2$ are combined to form a double bond, the N-substituted cyclic imido group may be formed together with the double bond. When $R^1$ and $R^2$ are combined to form an aromatic or non-aromatic ring, the N-substituted cyclic imido group may be formed with the adjacent two carbon atoms constituting the ring.

Preferred imide compounds include compounds of the following formulae:

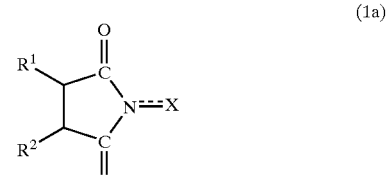
(1a)

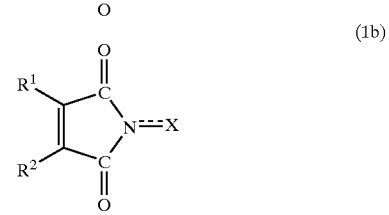
(1b)

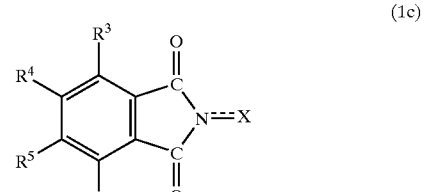
(1c)

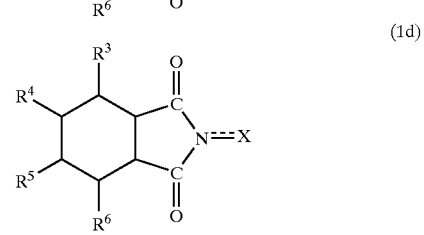
(1d)

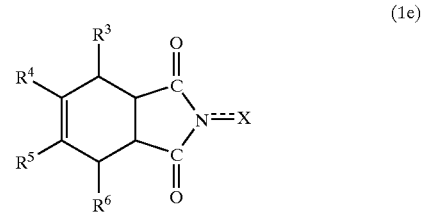
(1e)

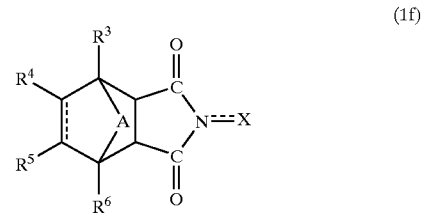
(1f)

wherein $R^3$, $R^4$, $R^5$ and $R^6$ are the same or different and are each a hydrogen atom, an alkyl group, a haloalkyl group, a hydroxyl group, an alkoxy group, a carboxyl group, an alkoxycarbonyl group, an acyl group, a nitro group, a cyano group, an amino group, or a halogen atom, where adjacent groups of $R^3$ to $R^6$ may be combined to form an aromatic or non-aromatic ring; A in Formula (1f) is a methylene group or an oxygen atom; and $R^1$, $R^2$ and X have the same meanings as defined above, and wherein one or two of the N-substituted cyclic imido group indicated in Formula (1c) may be further formed on the benzene ring in Formula (1c).

In the substituents $R^3$ to $R^6$, the alkyl group includes similar alkyl groups to those exemplified above, of which alkyl groups each containing from about 1 to about 6 carbon atoms are preferred. The haloalkyl group includes trifluoromethyl group, and other haloalkyl groups each containing from about 1 to about 4 carbon atoms. The alkoxy group includes similar alkoxy groups to those mentioned above, of which lower alkoxy groups each containing from about 1 to about 4 carbon atoms are preferred. The alkoxycarbonyl group includes similar alkoxycarbonyl groups to those described above, of which lower alkoxycarbonyl groups each containing from about 1 to about 4 carbon atoms in the alkoxy moiety are preferred. The acyl group includes similar acyl groups to those described above, of which acyl groups each containing from about 1 to about 6 carbon atoms are preferred. The halogen atom includes, for example, fluorine, chlorine and bromine atoms. Each of the substituents $R^3$ to $R^6$ is often a hydrogen atom, a lower alkyl group containing from about 1 to about 4 carbon atoms, a carboxyl group, a nitro group, or a halogen atom. The ring formed by $R^3$ to $R^6$ includes similar rings to the aforementioned rings which are formed by $R^1$ and $R^2$. Among them, aromatic or non-aromatic 5- to 12-membered rings are preferred.

Typical examples of preferred imide compounds are N-hydroxysuccinimide, N-hydroxy-α-methylsuccinimide, N-hydroxy-α,α-dimethylsuccinimide, N-hydroxymaleimide, N-hydroxyhexahydrophthalimide, N,N'-dihydroxycyclohexanetetracarboxylic imide, N-hydroxyphthalimide, N-hydroxytetrabromophthalimide, N-hydroxytetrachlorophthalimide, N-hydroxychlorendimide, N-hydroxyhimimide, N-hydroxytrimellitimide, N,N'-dihydroxypyromellitic imide, N,N'-dihydroxynaphthalenetetracarboxylic imide, and other compounds wherein X is an —OR group and R is a hydrogen atom; N-acetoxysuccinimide, N-acetoxymaleimide, N-acetoxyhexahydrophthalimide, N,N'-diacetoxycyclohexanetetracaboxylic imide, N-acetoxyphthalimide, N-acetoxytetrabromophthalimide, N-acetoxytetrachlorophthalimide, N-acetoxychlorendimide, N-acetoxyhimimide, N-acetoxytrimellitimide, N,N'-diacetoxypyromellitic imide, N,N'-diacetoxynaphthalenetetracarboxylic imide, N-benzoyloxyphthalimide, and other compounds wherein X is an —OR group and R is an acyl group such as acetyl group; N-methoxymethyloxyphthalimide, N-(2-methoxyethoxymethyloxy)phthalimide, and other compounds wherein X is an —OR group and R is a group that can form an acetal or hemiacetal bond with a hydroxyl group; N-methanesulfonyloxyphthalimide, N-(p-toluenesulfonyloxy)phthalimide, and other compounds wherein X is an —OR group and R is a sulfonyl group; sulfuric esters, nitric esters, phosphoric esters, and boric esters of N-hydroxyphthalimide, and other compounds wherein X is an —OR group and R is a group derived from an inorganic acid by removal of OH group.

Among them, typically preferred is N-hydroxysuccinimide which may have an alkyl group, such as methyl, ethyl or another $C_1$–$C_4$ alkyl group, at the α-position and/or the β-position and whose hydroxyl group may be protected by a protecting group such as acetoxy group or another acyl group. In general, oxidative cleavage of a cycloalkane with oxygen yields or by-produces a dicarboxylic acid having carbon atoms in its principle chain in a number equal to or less than the number of carbon atoms constituting the material cycloalkane. For example, cyclohexane yields glutaric acid and/or succinic acid in addition to adipic acid. In contrast, the imide compound used as the catalyst often undergoes ring-opening and is thereby decomposed into a corresponding dicarboxylic acid during the reaction. When the aforementioned N-hydroxysuccinimide or its analogue is used as the catalyst, the catalyst will yield a similar compound, such as succinic acid, to the reaction products even when it is decomposed. Accordingly, there is no need of a special step for removing such a decomposed product of the imide compound catalyst, and the process is industrially very advantageous.

Among the imide compounds, compounds wherein X is an —OR group and R is a hydrogen atom can be prepared by a conventional imidization process such as a process that comprises the steps of allowing a corresponding acid anhydride to react with hydroxylamine $NH_2OH$ for ring-opening of an acid anhydride group, and closing the ring to form an imide. Such acid anhydrides include succinic anhydride, maleic anhydride, and other saturated or unsaturated aliphatic dicarboxylic anhydrides, tetrahydrophthalic anhydride, hexahydrophthalic anhydride (1,2-cyclohexanedicarboxylic anhydride), 1,2,3,4-cyclohexanetetracarboxylic 1,2-dianhydride, and other saturated or unsaturated non-aromatic cyclic polycarboxylic anhydrides (alicyclic polycarboxylic anhydrides), HET anhydride(chlorendic anhydride), himic anhydride, and other bridged polycarboxylic anhydrides (alicyclic polycarboxylic anhydrides), phthalic anhydride, tetrabromophthalic anhydride, tetrachlorophthalic anhydride, nitrophthalic anhydride, trimellitic anhydride, methylcyclohexenetricarboxylic anhydride, pyromellitic anhydride, mellitic anhydride, 1,8;4,5-naphthalenetetracarboxylic dianhydride, and other aromatic polycarboxylic anhydrides.

Among the imide compounds, compounds wherein X is an —OR group and R is a hydroxyl-protecting group can be prepared by introducing a desired protecting group into a corresponding compound wherein R is a hydrogen atom (N-hydroxy cyclic imide compounds) by the aid of a conventional reaction for the introduction of protecting groups. For example, N-acetoxyphthalimide can be prepared by allowing N-hydroxyphthalimide to react with acetic anhydride or to react with an acetyl halide in the presence of a base.

Specifically preferred imide compounds are N-hydroxysuccinimide, N-hydroxyphthalimide, N,N'-dihydroxypyromellitimide, and other N-hydroxyimide compounds derived from aliphatic dicarboxylic anhydrides, alicyclic polycarboxylic anhydrides or aromatic polycarboxylic anhydrides, of which those derived from aliphatic dicarboxylic anhydrides or aromatic polycarboxylic anhydrides are especially preferred; and compounds obtained by introducing a protecting group into the hydroxyl group of these N-hydroxyimide compounds.

Each of the imide compounds having the N-substituted cyclic imide skeleton represented by Formula (I) can be used alone or in combination in the reaction. The imide compounds can be formed in the reaction system.

The imide compounds can be used as being supported by a carrier. Activated carbon, zeolite, silica, silica-alumina, bentonite, and other porous carries are often used as the carrier. The amount of the imide compound on the carrier is, for example, from about 0.1 to about 50 parts by weight, preferably from about 0.5 to about 30 parts by weight, and more preferably from about 1 to about 20 parts by weight, relative to 100 parts by weight of the carrier.

The amount of the imide compound can be selected within broad ranges and is, for example, from about 0.000001 to about 1 mole per mole of the substrate (from 0.0001% to 100% by mole) However, in consideration of economical efficiency and after-treatment, the amount of the imide compound is, per mole of the substrate, preferably from about 0.000001 to about 0.01 more (from about 0.0001% to about 1% by mole) and more preferably from about 0.00001 to about 0.005 mole (from about 0.001% to about 0.5% by mole). This is because a high space time yield can be obtained even using a small amount of the catalyst in the present invention.

[Metallic Compounds]

Metallic elements constituting metallic compounds for use as the catalyst are not specifically limited and are often metallic elements of the Groups 2 to 15 of the Periodic Table. The term "metallic element" as used herein also includes boron B. Examples of the metallic elements include, of the Periodic Table, Group 2 elements (e.g., Mg, Ca, Sr and Ba), Groups 3 elements (e.g., Sc, lanthanoid elements and actinoid elements), Group 4 elements (e.g., Ti, Zr and Hf), Group 5 elements (e.g., V), Group 6 elements (e.g., Cr, Mo and W), Group 7 elements (e.g., Mn), Group 8 elements (e.g., Fe and Ru), Group 9 elements (e.g., Co and Rh), Group 10 elements (e.g., Ni, Pd and Pt), Group 11 elements (e.g., Cu), Group 12 elements (e.g., Zn), Groups 13 elements (e.g., B, Al and In), Group 14 elements (e.g., Sn and Pb), and Group 15 elements (e.g., Sb and Bi). Preferred metallic elements include transition metal elements (elements of Groups 3 to 12 of the Periodic Table) and Group 13 elements of the Periodic Table. Among them, elements of the Groups 5 to 11 of the Periodic Table, such as V, Mo, Mn, Fe, Ru, Co, and Cu, are preferred, of which Mn, Fe, Co, and Cu are especially preferred. Above all, Co is preferred. The valence of the metallic element is not specifically limited and is, for example, from about 0 to about 6.

Such metallic compounds include, but are not limited to, elementary substances, hydroxides, oxides (including complex oxides), halides (fluorides, chlorides, bromides, and iodides), salts of oxoacids (e.g., nitrates, sulfates, phosphates, borates, and carbonates), salts of isopolyacids, salts of heteropolyacids, and other inorganic compounds of the aforementioned metallic elements; salts of organic acids (e.g., acetates, propionates, prussiates, naphthenates, stearates, and lactates), complexes, and other organic compounds of the metallic elements. Ligands constituting the complexes include OH (hydroxo), alkoxy (e.g., methoxy, ethoxy, propoxy, and butoxy), acyls (e.g., acetyl and propionyl), alkoxycarbonyls (e.g., methoxycarbonyl and ethoxycarbonyl), acetylacetonato, cyclopentadienyl group, halogen atoms (e.g., chlorine and bromine), CO, CN, oxygen atom, $H_2O$ (aquo), phosphines (triphenylphosphine and other triarylphosphines) and other phosphorus compounds, $NH_3$ (ammine), NO, $NO_2$ (nitro), $NO_3$ (nitrato), ethylenediamine, diethylenetriamine, pyridine, phenanthroline, and other nitrogen-containing compounds.

Specific examples of the metallic compounds include, by taking cobalt compounds as an example, cobalt hydroxide, cobalt oxide, cobalt chloride, cobalt bromide, cobalt nitrate, cobalt sulfate, cobalt phosphate, and other inorganic compounds; cobalt acetate, cobalt naphthenate, cobalt stearate, cobalt lactate, and other salts of organic acids; acetylacetonatocobalt, and other complexes, and other divalent or trivalent cobalt compounds. Examples of vanadium compounds include, but are not limited to, vanadium hydroxide, vanadium oxide, vanadium chloride, vanadyl chloride, vanadium sulfate, vanadyl sulfate, sodium vanadate, and other inorganic compounds; acetylacetonatovanadium, vanadyl acetylacetonato, and other complexes, and other vanadium compounds having a valence of from 2 to 5. Examples of compounds of the other metallic elements include compounds corresponding to the above-mentioned cobalt or vanadium compounds.

Each of these metallic compounds can be used alone or in combination. A combination use of a low-valence metallic compound with a high-valence metallic compound as the metallic compound may significantly increase the reaction rate as compared with the single use of each compound. When a metal may have plural valences, a metallic compound having a lower valence is called a "low-valence metallic compound" and a metallic compound having a higher valence is called a "high-valence metallic compound".

Examples of such combinations of a low-valence metallic compound with a high-valence metallic compound are combinations of a low-valence metallic compound selected from divalent cobalt compounds, divalent manganese compounds, divalent iron compounds and monovalent copper compounds with a high-valence metallic compound selected from trivalent cobalt compounds, trivalent manganese compounds, trivalent iron compounds, and divalent copper compounds. Among these combinations, those containing at least a divalent or trivalent cobalt compound are preferred, of which those of a divalent cobalt compound with a trivalent cobalt compound are especially preferred.

A combination use of two or more of metallic compounds containing different metallic elements may improve the conversion and/or selectivity as compared with a single use of each metallic compound. Such combinations include, for example, a combination of a cobalt compound (a divalent or trivalent cobalt compound) with a manganese compound (divalent or trivalent). In this case, the molar ratio of the cobalt compound to the manganese compound is, for example, from about 1:99 to about 99:1 and preferably from about 5:95 to about 95:5.

The amount of the metallic compound is, for example, from about 0.05 to about 20 moles, and preferably from about 0.1 to about 10 moles per mole of the imide compound.

[Promoters (Co-catalysts)]

Organic salts each comprising a polyatomic cation or a polyatomic anion and its counter ion, which polyatomic cation or anion contains a Group 15 or Group 16 element of the Periodic Table having at least one organic group combined therewith, can be used as a promoter (co-catalyst) in the present invention. By using the organic salts as the promoter, the rate and selectivity of the reaction can be improved.

In the organic salts, the Group 15 elements of the Periodic Table include N, P, As, Sb, and Bi, and the Group 16 elements of the Periodic Table include, for example, O, S, Se and Te. Preferred elements are N, P, As, Sb and S, of which N, P and S are typically preferred.

The organic groups to be combined with atoms of the elements include, but are not limited to, hydrocarbon groups which may have a substituent, and substituted oxy groups. The hydrocarbon groups include, but are not limited to, methyl, ethyl, propyl, isopropyl, butyl, isobutyl, s-butyl, t-butyl, pentyl, hexyl, octyl, decyl, tetradecyl, hexadecyl, octadecyl, allyl, and other straight- or branched-chain aliphatic hydrocarbon groups (alkyl groups, alkenyl groups and alkynyl groups) each containing from about 1 to about 30 carbon atoms (preferably from about 1 to about 20 carbon atoms); cyclopentyl, cyclohexyl, and other alicyclic hydrocarbon groups each containing from about 3 to about 8 carbon atoms; and phenyl, naphthyl, and other aromatic hydrocarbon groups each containing from about 6 to about 14 carbon atoms. Substituents which the hydrocarbon groups may have include, but are not limited to, halogen atoms, oxo group, hydroxyl group, substituted oxy groups (e.g., alkoxy groups, aryloxy groups, and acyloxy groups), carboxyl group, substituted oxycarbonyl groups, substituted or unsubstituted carbamoyl groups, cyano group, nitro group, substituted or unsubstituted amino groups, alkyl groups (e.g., methyl, ethyl, and other $C_1$–$C_4$ alkyl groups), cycloalkyl groups, aryl groups (e.g., phenyl and naphthyl groups), and heterocyclic groups. The preferred hydrocarbon groups include, for example, alkyl groups each containing from about 1 to about 30 carbon atoms, and aromatic hydrocarbon groups (especially, phenyl or naphthyl group) each containing from about 6 to about 14 carbon atoms. The substituted oxy groups include, but are not limited to, alkoxy groups, aryloxy groups and aralkyloxy groups.

Typical examples of the organic salts include organic ammonium salts, organic phosphonium salts, organic sulfonium salts, and other organic onium salts. Examples of the organic ammonium salts are tetramethylammonium chloride, tetraethylammonium chloride, tetrabutylammonium chloride, tetrahexylammonium chloride, trioctylmethylammonium chloride, triethylphenylammonium chloride, tributyl(hexadecyl)ammonium chloride, di(octadecyl)dimethylammonium chloride, and other quaternary ammonium chlorides, and corresponding quaternary ammonium bromides, and other quaternary ammonium salts each containing four hydrocarbon groups combined with a nitrogen atom; dimethylpiperidinium chloride, hexadecylpyridinium chloride, methylquinolinium chloride, and other cyclic quaternary ammonium salts. Examples of the organic phosphonium salts are tetramethylphosphonium chloride, tetrabutylphosphonium chloride, tributyl (hexadecyl)phosphonium chloride, triethylphenylphosphonium chloride, and other quaternary phosphonium chlorides, corresponding quaternary phosphonium bromides, and other quaternary phosphonium salts each containing four hydrocarbon groups combined with a phosphorus atom. Examples of the organic sulfonium salts are triethylsulfonium iodide, ethyldiphenylsulfonium iodide, and other sulfonium salts each containing three hydrocarbon groups combined with a sulfur atom.

The organic salts also include methanesulfonates, ethanesulfonates, octanesulfonates, dodecanesulfonates, and other alkyl-sulfonates (e.g., $C_1$–$C_{18}$ alkyl-sulfonates); benzenesulfonates, p-toluenesulfonates, naphthalenesulfonates, decylbenzenesulfonates, dodecylbenzenesulfonates, and other aryl-sulfonates which may be substituted with an alkyl group (e.g., $C_1$–$C_{18}$ alkyl-arylsulfonates); sulfonic acid type ion exchange resins (ion exchangers); and phosphonic acid type ion exchange resins (ion exchangers).

The amount of the organic salt is, for example, from about 0.001 to about 20 moles, and preferably from about 0.1 to about 10 moles per mole of the imide compound.

The system in the process of the present invention may further comprise a free-radical generator or a free-radical reaction accelerator. Such components include, but are not limited to, halogens (e.g., chlorine and bromine), peracids (e.g., peracetic acid and m-chloroperbenzoic acid), and peroxides (e.g., hydrogen peroxide, t-butyl hydroperoxide (TBHP), and other hydroperoxides), as well as nitric acid, nitrous acid, and salts thereof. The existence of the component(s) in the system may enhance the reaction. The amount of the aforementioned component(s) is, for example, from about 0.001 to about 20 moles per mole of the imide compound.

[Reactions]

The reaction is performed in the presence of a solvent. Such solvents include, but are not limited to, benzene and other aromatic hydrocarbons; dichloromethane, chloroform, 1,2-dichloroethane, dichlorobenzene, and other halogenated hydrocarbons; t-butyl alcohol, t-amyl alcohol, and other alcohols; acetonitrile, benzonitrile, and other nitrites; acetic acid, propionic acid, and other organic acids; formamide, acetamide, dimethylformamide (DMF), dimethylacetamide, and other amides. These solvents can be used in combination. Among the solvents, organic acids and other organic protic solvents as well as nitrites are preferred. The reaction product dicarboxylic acid can also serve as a reaction solvent.

An important feature of the present invention is that the reaction is performed under conditions of a reaction temperature of 80° C. or higher and a concentration of the cycloalkane in the reaction system of 21% by weight or higher (from 21% to 100% by weight). The reaction temperature is, for example, from about 80° C. to about 200° C., preferably from about 80° C. to about 150° C., and especially preferably from about 90° C. to about 140° C. If the reaction temperature is lower than 80° C., the reaction rate is markedly decreased. The concentration of the cycloalkane is preferably from about 21% to about 99.5% by weight, more preferably from about 25% to about 95% by weight (e.g., from 35% to 95% by weight), further preferably from about 30% to about 70% by weight (e.g., from 35% to 70% by weight), and typically preferably from about 35% to about 55% by weight (e.g., from 40% to 55% by weight).

If the concentration of the cycloalkane in the reaction system is excessively low, i.e., less than 21% by weight, the conversion rate from the cycloalkane is low and the space time yield of the resulting dicarboxylic acid is markedly low. Namely, the yield of the dicarboxylic acid per unit volume and unit time is low, and the dicarboxylic acid cannot be obtained with high production efficiency. In contrast, when the substrate concentration falls within the above-specified range, the conversion rate of the cycloalkane is high and the corresponding dicarboxylic acid can be obtained in a high space time yield. Although reasons are not completely clarified, this is probably because, when the concentration of the cycloalkane is excessively low, the rate of a reaction (key step in chain steps) decreases, in which reaction a radical (peroxy radical) formed in the system withdraws a hydrogen from the substrate cycloalkane, and therefore the reaction rate as a whole decreases.

In this connection, the space time yield of the dicarboxylic acid increases with an increasing concentration of the cycloalkane in the reaction system, but passes through the maximum and gradually decreases when the concentration of the cycloalkane reaches a certain level or higher. Although reasons are not completely clarified, this is probably because the solubility of the catalyst decreases and thereby the reaction rate also decreases at a very high concentration of the cycloalkane.

The reaction can be performed at normal pressure or under a pressure (under a load). When the reaction is performed under a pressure (under a load), the reaction pressure is, for example, from about 0.5 to about 20 MPa, and preferably from about 1 to about 15 MPa.

The reaction can be performed in the presence of, or under the flow of, oxygen according to a conventional procedure such as a batch system, semi-batch system or continuous system. When the reaction is performed in the batch system or semi-batch system, good results can be obtained by setting the initial concentration of the cycloalkane within the above-specified range (21% by weight or higher). When the reaction is performed in the continuous system, the dicarboxylic acid can be obtained with a high production efficiency by setting the concentration of the cycloalkane in a steady state within the above-specified range (21% by weight or higher).

In the present invention, the cycloalkane used as a raw material oxidatively cleaves and thereby yields a dicarboxylic acid having a carbon chain containing carbon atoms in the same number as that of carbon atoms constituting the cycloalkane ring. Specifically, cyclohexane yields adipic acid, and cyclododecane yields a dodecanedioic acid. Under some conditions, a dicarboxylic acid having a carbon chain containing carbon atoms in a number one or two less than the number of carbon atoms constituting the cycloalkane ring, a corresponding cycloalkanol, a cycloalkanone, and other products may be by-produced. For example, when cyclohexane is used as a raw material, glutaric acid, succinic acid, cyclohexanol, and/or cyclohexanone may be by-produced. Among these by-products, cycloalkanols and cyclohexanone can be recycled to the reaction system.

After the completion of the reaction, reaction products can be separated and purified by a separation means such as filtration, concentration, distillation, extraction, crystallization, recrystallization, adsorption, and column chromatography or any combination of these separation means.

INDUSTRIAL APPLICABILITY

Dicarboxylic acids obtained by the production process of the present invention can be used, for example, as raw materials for polyamides (nylons) and polyesters and as intermediate materials for fine chemicals.

In the production of a corresponding dicarboxylic acid by catalytic oxidation of a cycloalkane with oxygen, the present invention can produce the dicarboxylic acid in a high space time yield even using a small amount of a catalyst.

EXAMPLES

The present invention will be illustrated in further detail with reference to several examples below, which are not intended to limit the scope of the invention.

Analysis of Products

Other components such as cyclohexane, cyclohexanone, and cyclohexanol than dicarboxylic acids were analyzed by bringing a reaction mixture directly into a gas chromatograph.

The dicarboxylic acids such as adipic acid, glutaric acid and succinic acid were analyzed by converting a target dicarboxylic acid into a dimethyl ester derivative in the following manner and analyzing the dimethyl ester derivative by gas chromatography. Specifically, about 1 g of the reaction mixture was sampled, a solvent therein was removed by distillation using an evaporator, the residue was diluted with about 1 g of methanol, and a commercially available TMS-CHN$_2$ was added to the mixture until the mixture became yellow, and the resulting mixture was stirred for about 1 hour. Next, acetic acid was added to the mixture until the mixture became colorless, the resulting mixture was brought into a gas chromatograph and was analyzed.

Gas Chromatography (GC) Conditions
  Model: 14A available from Shimadzu Corporation
  Detector: FID
  Column: FEAP (25 m×0.32 mm×0.25 μm)
  Temperature Conditions:
  INJ, DET: 280° C.
  Column: The column was held at 50° C. for 5 minutes and was raised in temperature to 150° C. at a rate of 5° C. per minute.
  Gas flow rate: 2.8 ml/min, split ratio: 50

Example 1

In a 316 stainless steel reactor having an internal volume of 300 ml, 26 g (309 mmol) of cyclohexane, 14 g of acetic acid, 100.9 mg (0.618 mmol) of N-hydroxyphthalimide, 76.9 mg (0.309 mmol) of cobalt(II) acetate tetrahydrate, and 110 mg (0.309 mmol) of bis (acetylacetonato) cobalt(II) were placed, and the reactor was sealed and was pressurized to 50 Kg/cm$^2$ (4.9 MPa) with a gaseous mixture comprising 50% Of O$_2$ and 50% of N$_2$. The liquid temperature was raised on an oil bath and was held at 110° C. Immediately after the liquid temperature reached 110° C., absorption of the gas began. The reaction was terminated by cooling 20 minutes later. A reaction mixture was diluted with 60 g of acetic acid to thereby dissolve all of solid matters. The resulting solution was analyzed to find that a conversion from cyclohexane was 24.4% and a selectivity for adipic acid was 56.1%. In addition, glutaric acid (selectivity: 14.3%), succinic acid (selectivity: 12.1%), cyclohexanone (selectivity: 10.9%), cyclohexanol (selectivity: 5.9%), and cyclohexyl acetate (selectivity: 0.71%) were by-produced.

Example 2

In a 316 stainless steel reactor having an internal volume of 300 ml, 18 g (214 mmol) of cyclohexane, 22 g of acetic acid, 69.7 mg (0.428 mmol) of N-hydroxyphthalimide, 53.3 mg (0.214 mmol) of cobalt(II) acetate tetrahydrate, and 76.2 mg (0.214 mmol) of tris(acetylacetonato) cobalt(III) were placed, and the reactor was sealed and was pressurized to 50 Kg/cm$^2$ (4.9 MPa) with a gaseous mixture comprising 50% of O$_2$ and 50% of N$_2$. The liquid temperature was raised on an oil bath and was held at 110° C. Immediately after the liquid temperature reached 110° C., absorption of the gas began. The reaction was terminated by cooling 20 minutes later. A reaction mixture was diluted with 60 g of acetic acid to thereby dissolve all of solid matters. The resulting solution was analyzed to find that a conversion from cyclohexane was 64.8% and a selectivity for adipic acid was 71.6%. In addition, glutaric acid (selectivity: 13.0%), succinic acid (selectivity: 12.5%), cyclohexanone (selectivity: 2.1%), cyclohexanol (selectivity: 1.7%), and cyclohexyl acetate (selectivity: 0.29%) were by-produced.

Example 3

In a 316 stainless steel reactor having an internal volume of 300 ml, 36 g (428 mmol) of cyclohexane, 4 g of acetic acid, 139.7 mg (0.856 mmol) of N-hydroxyphthalimide, 106.6 mg (0.428 mmol) of cobalt(II) acetate tetrahydrate, and 152.5 mg (0.428 mmol) of tris(acetylacetonato) cobalt (III) were placed, and the reactor was sealed and was pressurized to 50 Kg/cm$^2$ (4.9 MPa) with a gaseous mixture comprising 50% of O$_2$ and 50% of N$_2$. The liquid temperature was raised on an oil bath and was held at 110° C. Immediately after the liquid temperature reached 110° C., absorption of the gas began. The reaction was terminated by cooling 20 minutes later. A reaction mixture was diluted with 60 g of acetic acid to thereby dissolve all of solid matters. The resulting solution was analyzed to find that a conversion from cyclohexane was 8.3% and a selectivity for adipic acid was 36.4%. In addition, glutaric acid (selectivity: 10.4%), succinic acid (selectivity: 7.7%), cyclohexanone (selectivity: 22.6%), cyclohexanol (selectivity: 21.6%), and cyclohexyl acetate (selectivity: 1.4%) were by-produced.

Example 4

In a 316 stainless steel reactor having an internal volume of 300 ml, 39.6 g (470 mmol) of cyclohexane, 0.4 g of acetic acid, 153.5 mg (0.940 mmol) of N-hydroxyphthalimide, 117.2 mg (0.470 mmol) of cobalt(II) acetate tetrahydrate, and 167.8 mg (0.470 mmol) of tris (acetylacetonato) cobalt (III) were placed, and the reactor was sealed and was pressurized to 50 Kg/cm$^2$ (4.9 MPa) with a gaseous mixture comprising 50% of O$_2$ and 50% of N$_2$. The liquid temperature was raised on an oil bath and was held at 110° C. Immediately after the liquid temperature reached 110° C., absorption of the gas began. The reaction was terminated by cooling 60 minutes later. A reaction mixture was diluted with 60 g of acetic acid to thereby dissolve all of solid matters. The resulting solution was analyzed to find that a conversion from cyclohexane was 6.9% and a selectivity for adipic acid was 14.9%. In addition, glutaric acid (selectivity: 4.5%), succinic acid (selectivity: 3.9%), cyclohexanone (selectivity: 40.6%), cyclohexanol (selectivity: 35.5%), and cyclohexyl acetate (selectivity: 0.5%) were by-produced.

Example 5

In a 316 stainless steel reactor having an internal volume of 300 ml, 12 g (142 mmol) of cyclohexane, 28 g of acetic acid, 46.53 mg (0.285 mmol) of N-hydroxyphthalimide, 35.49 mg (0.143 mmol) of cobalt(II) acetate tetrahydrate, and 50.75 mg (0.143 mmol) of tris(acetylacetonato) cobalt (III) were placed, and the reactor was sealed and was pressurized to 50 Kg/cm$^2$ (4.9 MPa) with a gaseous mixture comprising 50% of O$_2$ and 50% of N$_2$. The liquid temperature was raised on an oil bath and was held at 110° C. Immediately after the liquid temperature reached 110° C., absorption of the gas began. The reaction was terminated by cooling 60 minutes later. A reaction mixture was diluted with 60 g of acetic acid to thereby dissolve all of solid matters. The resulting solution was analyzed to find that a conversion from cyclohexane was 13.5% and a selectivity for adipic acid was 61.0%. In addition, glutaric acid (selectivity: 12.2%), succinic acid (selectivity: 11.8%), cyclohexanone (selectivity: 7.7%), cyclohexanol (selectivity: 5.8%), and cyclohexyl acetate (selectivity: 1.5%) were by-produced.

Comparative Example 1

In a 316 stainless steel reactor having an internal volume of 300 ml, 10 g (118 mmol) of cyclohexane, 40 g of acetic acid, 38.8 mg (0.237 mmol) of N-hydroxyphthalimide, 29.6 mg (0.118 mmol) of cobalt(II) acetate tetrahydrate, and 42.4 mg (0.118 mmol) of tris(acetylacetonato) cobalt(III) were placed, and the reactor was sealed and was pressurized to 50 Kg/cm$^2$ (4.9 MPa) with a gaseous mixture comprising 50% of O$_2$ and 50% of N$_2$. The liquid temperature was raised on an oil bath and was held at 110° C. Immediately after the liquid temperature reached 110° C., absorption of the gas began. The reaction was terminated by cooling 60 minutes later. A reaction mixture was analyzed to find that a conversion from cyclohexane was 1.8% and adipic acid was not produced. In addition, cyclohexanone (selectivity: 57.8%), cyclohexanol (selectivity: 33.0%), and cyclohexyl acetate (selectivity: 9.3%) were produced.

Example 6

In a 316 stainless steel reactor having an internal volume of 300 ml, 52 g (618 mmol) of cyclohexane, 28 g of acetic acid, 50.5 mg (0.309 mmol) of N-hydroxyphthalimide, 38.5 mg (0.154 mmol) of cobalt(II) acetate tetrahydrate, and 55.0 mg (0.154 mmol) of tris(acetylacetonato) cobalt(III) were placed, and the reactor was sealed and was pressurized to 50 Kg/cm$^2$ (4.9 MPa) with a gaseous mixture comprising 50% of O$_2$ and 50% of N$_2$. The liquid temperature was raised on an oil bath and was held at 110° C. Immediately after the liquid temperature reached 110° C., absorption of the gas began. The reaction was terminated by cooling 20 minutes later. A reaction mixture was diluted with 60 g of acetic acid to thereby dissolve all of solid matters. The resulting solution was analyzed to find that a conversion from cyclohexane was 21.7% and a selectivity for adipic acid was 57.0%. In addition, glutaric acid (selectivity: 9.37%), succinic acid (selectivity: 8.37%), cyclohexanone (selectivity: 15.2%), cyclohexanol (selectivity: 9.4%), and cyclohexyl acetate (selectivity: 0.69%) were by-produced.

Example 7

In a 316 stainless steel reactor having an internal volume of 300 ml, 52 g (618 mmol) of cyclohexane, 28 g of acetic acid, 25.3 mg (0.154 mmol) of N-hydroxyphthalimide, 19.2 mg (0.077 mmol) of cobalt(II) acetate tetrahydrate, and 27.4 mg (0.077 mmol) of tris(acetylacetonato) cobalt(III) were placed, and the reactor was sealed and was pressurized to 50 Kg/cm$^2$ (4.9 MPa) with a gaseous mixture comprising 50% of O$_2$ and 50% of N$_2$. The liquid temperature was raised on an oil bath and was held at 110° C. Immediately after the liquid temperature reached 110° C., absorption of the gas began. The reaction was terminated by cooling 20 minutes later. A reaction mixture was diluted with 60 g of acetic acid to thereby dissolve all of solid matters. The resulting solution was analyzed to find that a conversion from cyclohexane was 20.5% and a selectivity for adipic acid was 55.4%. In addition, glutaric acid (selectivity: 10.1%), succinic acid (selectivity: 8.9%), cyclohexanone (selectivity: 14.2%), cyclohexanol (selectivity: 8.54%), and cyclohexyl acetate (selectivity: 2.94%) were by-produced.

Example 8

In a 316 stainless steel reactor having an internal volume of 300 ml, 18 g (214 mmol) of cyclohexane, 22 g of acetic acid, 69.7 mg (0.428 mmol) of N-hydroxyphthalimide, 5.33 mg (0.0214 mmol) of cobalt(II) acetate tetrahydrate, and 7.62 mg (0.0214 mmol) of tris(acetylacetonato) cobalt(III) were placed, and the reactor was sealed and was pressurized to 50 Kg/cm$^2$ (4.9 MPa) with a gaseous mixture comprising 50% of O$_2$ and 50% of N$_2$. The liquid temperature was raised on an oil bath and was held at 110° C. Immediately after the liquid temperature reached 110° C., absorption of the gas began. The reaction was terminated by cooling 60 minutes later. A reaction mixture was diluted with 60 g of acetic acid to thereby dissolve all of solid matters. The resulting solution was analyzed to find that a conversion from cyclohexane was 17.5% and a selectivity for adipic acid was 45.8%. In addition, glutaric acid (selectivity: 10.1%), succinic acid (selectivity: 7.4%), cyclohexanone (selectivity: 23.8%), cyclohexanol (selectivity: 11.1%), and cyclohexyl acetate (selectivity: 1.9%) were by-produced.

Example 9

In a 316 stainless steel reactor having an internal volume of 300 ml, 52 g (618 mmol) of cyclohexane, 28 g of acetic acid, 203.6 mg (1.236 mmol) of N-hydroxyphthalimide, and 441 mg (1.236 mmol) of tris (acetylacetonato) cobalt(III) were placed, and the reactor was sealed and was pressurized to 50 Kg/cm$^2$ (4.9 MPa) with a gaseous mixture comprising 50% of O$_2$ and 50% of N$_2$. The liquid temperature was raised on an oil bath and was held at 110° C. Immediately after the liquid temperature reached 110° C., absorption of the gas began. The reaction was terminated by cooling 60 minutes later. A reaction mixture was diluted with 120 g of acetic acid to thereby dissolve all of solid matters. The resulting solution was analyzed to find that a conversion from cyclohexane was 13.8% and a selectivity for adipic acid was 58.8%. In addition, glutaric acid (selectivity: 11.0%), succinic acid (selectivity: 10.9%), cyclohexanone (selectivity: 3.67%), cyclohexanol (selectivity: 14.6%), and cyclohexyl acetate (selectivity: 1.09%) were by-produced.

Example 10

In a 316 stainless steel reactor having an internal volume of 300 ml, 18 g (214 mmol) of cyclohexane, 22 g of acetic acid, 69.7 mg (0.428 mmol) of N-hydroxyphthalimide, 61.9 mg (0.214 mmol) of bis(acetylacetonato)manganese(II) dihydrate, and 75.4 mg (0.214 mmol) of tris(acetylacetonato)manganese(III) were placed, and the reactor was sealed and was pressurized to 50 Kg/cm$^2$ (4.9 MPa) with a gaseous mixture comprising 50% Of $O_2$ and 50% of $N_2$. The liquid temperature was raised on an oil bath and was held at 110° C. Immediately after the liquid temperature reached 110° C., absorption of the gas began. The reaction was terminated by cooling 60 minutes later. A reaction mixture was diluted with 60 g of acetic acid to thereby dissolve all of solid matters. The resulting solution was analyzed to find that a conversion from cyclohexane was 38.9% and a selectivity for adipic acid was 71.5%. In addition, glutaric acid (selectivity: 14.0%), succinic acid (selectivity: 9.3%), cyclohexanone (selectivity: 0.4%), cyclohexanol (selectivity: 3.9%), and cyclohexyl acetate (selectivity: 1.0%) were by-produced.

Example 11

In a 316 stainless steel reactor having an internal volume of 300 ml, 18 g (214 mmol) of cyclohexane, 22 g of acetic acid, 69.7 mg (0.428 mmol) of N-hydroxyphthalimide, 61.6 mg (0.214 mmol) of iron(II) lactate [ferrous lactate], and 75.5 mg (0.214 mmol) of tris(acetylacetonato)iron(III) were placed, and the reactor was sealed and was pressurized to 50 Kg/cm$^2$ (4.9 MPa) with a gaseous mixture comprising 50% of $O_2$ and 50% of $N_2$. The liquid temperature was raised on an oil bath and was held at 110° C. Immediately after the liquid temperature reached 110° C., absorption of the gas began. The reaction was terminated by cooling 60 minutes later. A reaction mixture was diluted with 60 g of acetic acid to thereby dissolve all of solid matters. The resulting solution was analyzed to find that a conversion from cyclohexane was 14.3% and a selectivity for adipic acid was 31.8%. In addition, glutaric acid (selectivity: 8.1%), succinic acid (selectivity: 9.9%), cyclohexanone (selectivity: 38.9%), cyclohexanol (selectivity: 10.0%), and cyclohexyl acetate (selectivity: 1.4%) were by-produced.

Example 12

In a 316 stainless steel reactor having an internal volume of 300 ml, 18 g (214 mmol) of cyclohexane, 22 g of acetic acid, 69.7 mg (0.428 mmol) of N-hydroxyphthalimide, 21.2 mg (0.214 mmol) of copper(I) chloride, and 42.7 mg (0.214 mmol) of copper(II) acetate were placed, and the reactor was sealed and was pressurized to 50 Kg/cm$^2$ (4.9 MPa) with a gaseous mixture comprising 50% of $O_2$ and 50% of $N_2$. The liquid temperature was raised on an oil bath and was held at 110° C. Immediately after the liquid temperature reached 110° C., absorption of the gas began. The reaction was terminated by cooling 60 minutes later. A reaction mixture was diluted with 60 g of acetic acid to thereby dissolve all of solid matters. The resulting solution was analyzed to find that a conversion from cyclohexane was 13.0% and a selectivity for adipic acid was 38.8%. In addition, glutaric acid (selectivity: 9.4%), succinic acid (selectivity: 8.4%), cyclohexanone (selectivity: 29.5%), cyclohexanol (selectivity: 11.8%), and cyclohexyl acetate (selectivity: 2.1%) were by-produced.

Example 13

In a 316 stainless steel reactor having an internal volume of 300 ml, 18 g (214 mmol) of cyclohexane, 22 g of acetic acid, 69.7 mg (0.428 mmol) of N-hydroxyphthalimide, 212 mg (2.14 mmol) of copper(I) chloride, and 427 mg (2.14 mmol) of copper(II) acetate were placed, and the reactor was sealed and was pressurized to 50 Kg/cm$^2$ (4.9 MPa) with a gaseous mixture comprising 50% of $O_2$ and 50% of $N_2$. The liquid temperature was raised on an oil bath and was held at 110° C. Immediately after the liquid temperature reached 110° C., absorption of the gas began. The reaction was terminated by cooling 60 minutes later. A reaction mixture was diluted with 60 g of acetic acid to thereby dissolve all of solid matters. The resulting solution was analyzed to find that a conversion from cyclohexane was 36.6% and a selectivity for adipic acid was 62.1%. In addition, glutaric acid (selectivity: 17.7%), succinic acid (selectivity: 12.7%), cyclohexanone (selectivity: 1.41%), cyclohexanol (selectivity: 4.90%), and cyclohexyl acetate (selectivity: 1.14%) were by-produced.

Example 14

In a 316 stainless steel reactor having an internal volume of 300 ml, 26 g (309 mmol) of cyclohexane, 14 g of acetic acid, 100.8 mg (0.617 mmol) of N-hydroxyphthalimide, 179 mg (0.617 mmol) of bis(acetylacetonato)manganese(II) dihydrate, and 15.4 mg (0.0617 mmol) of cobalt(II) acetate tetrahydrate were placed, and the reactor was sealed and was pressurized to 50 Kg/cm$^2$ (4.9 MPa) with a gaseous mixture comprising 50% of $O_2$ and 50% of $N_2$. The liquid temperature was raised on an oil bath and was held at 110° C. Immediately after the liquid temperature reached 110° C., absorption of the gas began. The reaction was terminated by cooling 60 minutes later. A reaction mixture was diluted with 60 g of acetic acid to thereby dissolve all of solid matters. The resulting solution was analyzed to find that a conversion from cyclohexane was 14.7% and a selectivity for adipic acid was 62.9%. In addition, glutaric acid (selectivity: 20.2%), succinic acid (selectivity: 5.5%), cyclohexanone (selectivity: 7.1%), cyclohexanol (selectivity: 3.3%), and cyclohexyl acetate (selectivity: 1.0%) were by-produced.

Example 15

In a 316 stainless steel reactor having an internal volume of 100 ml, 13.5 g (160 mmol) of cyclohexane, 16.5 g of acetonitrile, 52.3 mg (0.320 mmol) of N-hydroxyphthalimide, 57.1 mg (0.160 mmol) of tris(acetylacetonato) cobalt(III), and 39.9 mg (0.160 mmol) of cobalt(II) acetate were placed, and the reactor was sealed and was pressurized to 50 Kg/cm$^2$ (4.9 MPa) with a gaseous mixture comprising 50% of $O_2$ and 50% of $N_2$. The liquid temperature was raised on an oil bath and was held at 100° C. Immediately after the liquid temperature reached 100° C., absorption of the gas began. The reaction was terminated by cooling 60 minutes later. A reaction mixture was analyzed to find that a conversion from cyclohexane was 8.8% and a selectivity for adipic acid was 17.9%. In addition, glutaric acid (selectivity: 3.4%), succinic acid (selectivity: 1.7%), cyclohexanone (selectivity: 41.3%), cyclohexanol (selectivity: 35.3%), and cyclohexyl acetate (selectivity: 0.43%) were by-produced.

Comparative Example 2

In a 316 stainless steel reactor having an internal volume of 300 ml, 26 g (309 mmol) of cyclohexane, 14 g of acetic acid, 179 mg (0.617 mmol) of bis(acetylacetonato)manganese(II) dihydrate, and 15.4 mg (0.0617 mmol) of cobalt(II) acetate tetrahydrate were placed, and the reactor was sealed and was pressurized to 50 Kg/cm² (4.9 MPa) with a gaseous mixture comprising 50% of $O_2$ and 50% of $N_2$. The liquid temperature was raised on an oil bath and was held at 110° C. Immediately after the liquid temperature reached 110° C., absorption of the gas began. The reaction was terminated by cooling 60 minutes later. A reaction mixture was diluted with 60 g of acetic acid to thereby dissolve all of solid matters. The resulting solution was analyzed to find that a conversion from cyclohexane was 0.11% and adipic acid was not produced. In addition, cyclohexanone (selectivity: 28.2%), cyclohexanol (selectivity: 70.3%), and cyclohexyl acetate (selectivity: 1.5%) were produced.

Comparative Example 3

In a 316 stainless steel reactor having an internal volume of 300 ml, 26 g (309 mmol) of cyclohexane, 14 g of acetic acid, and 100.8 mg (0.617 mmol) of N-hydroxyphthalimide were placed, and the reactor was sealed and was pressurized to 50 Kg/cm² (4.9 MPa) with a gaseous mixture comprising 50% of $O_2$ and 50% of $N_2$. The liquid temperature was raised on an oil bath and was held at 110° C. Immediately after the liquid temperature reached 110° C., absorption of the gas began. The reaction was terminated by cooling 60 minutes later. A reaction mixture was diluted with 60 g of acetic acid to thereby dissolve all of solid matters. The resulting solution was analyzed to find that a conversion from cyclohexane was 0.23% and adipic acid was not produced. In addition, cyclohexanone (selectivity: 53.4%), cyclohexanol (selectivity: 46.1%), and cyclohexyl acetate (selectivity: 0.5%) were produced.

Example 16

In a flask having an internal volume of 100 ml, 8.4 g (50 mmol) of cyclododecane, 4.52 g of acetic acid, 16.3 mg (0.1 mmol) of N-hydroxyphthalimide, 28.9 mg (0.1 mmol) of bis(acetylacetonato)manganese(II) dihydrate, and 2.0 mg (0.01 mmol) of cobalt(II) acetate tetrahydrate were placed, and an oxygen balloon was attached to the reactor. The liquid temperature was raised on an oil bath and was held at 100° C. The reaction was terminated by cooling 6 hours later. A reaction mixture was diluted with 60 g of acetic acid to thereby dissolve all of solid matters. The resulting solution was analyzed to find that a conversion from cyclododecane was 20.6% and a selectivity for dodecanedioic acid was 23.7%. In addition, cyclododecanone (selectivity: 7.3%) and cyclododecanol (selectivity: 13.1%) were by-produced.

Example 17

In a flask having an internal volume of 100 ml, 8.4 g (50 mmol) of cyclododecane, 12.6 g of acetic acid, 16.3 mg (0.1 mmol) of N-hydroxyphthalimide, 28.9 mg (0.1 mmol) of bis(acetylacetonato)manganese(II) dihydrate, and 2.0 mg (0.01 mmol) of cobalt(II) acetate tetrahydrate were placed, and an oxygen balloon was attached to the reactor. The liquid temperature was raised on an oil bath and was held at 100° C. The reaction was terminated by cooling 4 hours later. A reaction mixture was diluted with 60 g of acetic acid to thereby dissolve all of solid matters. The resulting solution was analyzed to find that a conversion from cyclododecane was 26.5% and a selectivity for dodecanedioic acid was 21.4%. In addition, cyclododecanone (selectivity: 6.6%) and cyclododecanol (selectivity: 17.6%) were by-produced.

Example 18

In a flask having an inner volume of 100 ml, 8.4 g (50 mmol) of cyclododecane, 12.6 g of acetic acid, 32.6 mg (0.2 mmol) of N-hydroxyphthalimide, 57.8 mg (0.2 mmol) of bis(acetylacetonato)manganese(II) dihydrate, and 4.0 mg (0.02 mmol) of cobalt(II) acetate tetrahydrate were placed, and an oxygen balloon was attached to the reactor. The liquid temperature was raised on an oil bath and was held at 100° C. The reaction was terminated by cooling 4 hours later. A reaction mixture was diluted with 60 g of acetic acid to thereby dissolve all of solid matters. The resulting solution was analyzed to find that a conversion from cyclododecane was 16.1% and a selectivity for dodecanedioic acid was 27.5%. In addition, cyclododecanone (selectivity: 2.9%) and cyclododecanol (selectivity: 9.8%) were by-produced.

Example 19

In a 316 stainless steel reactor having an internal volume of 300 ml, 72 g (857 mmol) of cyclohexane, 351.4 mg (1.71 mmol) of N-acetoxyphthalimide, 214 mg (0.859 mmol) of cobalt(II) acetate tetrahydrate, and 306 mg (0.859 mmol) of tris(acetylacetonato) cobalt(III) were placed, and the reactor was sealed and was pressurized to 50 Kg/cm² (4.9 MPa) with a gaseous mixture comprising 50% of $O_2$ and 50% of $N_2$. The liquid temperature was raised on an oil bath and was held at 110° C. Immediately after the liquid temperature reached 110° C., absorption of the gas began. The reaction was terminated by cooling 60 minutes later. A reaction mixture was analyzed to find that a conversion from cyclohexane was 3.65% and a selectivity for adipic acid was 4.79%. In addition, glutaric acid (selectivity: 1.15%), succinic acid (selectivity: 0.60%), cyclohexanone (selectivity: 49.8%), and cyclohexanol (selectivity: 43.6%) were by-produced.

These results are shown in Tables 1 to 4. In the tables, the symbols "NHPI", "acac", "Ac", and "lac" mean N-hydroxyphthalimide, acetylacetone ligand, acetyl group, and lactic acid group, respectively. The term "mol %" after the names of imide compounds and metallic compounds indicates the ratio to a cycloalkane used as a raw material.

TABLE 1

|  | Ex. 1 | Ex. 2 | Ex. 3 | Ex. 4 | Ex. 5 | Ex. 19 | Com. Ex. 1 |
| --- | --- | --- | --- | --- | --- | --- | --- |
| Cyclohexane concentration (wt. %) | 65 | 45 | 90 | 99 | 30 | 100 | 20 |
| NHPI (mol %) | 0.2 | 0.2 | 0.2 | 0.2 | 0.2 | 0.2* | 0.2 |
| Co(acac)$_3$ (mol %) | 0.1 | 0.1 | 0.1 | 0.1 | 0.1 | 0.1 | 0.1 |
| Co(OAc)$_2$ (mol %) | 0.1 | 0.1 | 0.1 | 0.1 | 0.1 | 0.1 | 0.1 |
| Reaction temperature (° C.) | 110 | 110 | 110 | 110 | 110 | 110 | 110 |

TABLE 1-continued

|  | Ex. 1 | Ex. 2 | Ex. 3 | Ex. 4 | Ex. 5 | Ex. 19 | Com. Ex. 1 |
|---|---|---|---|---|---|---|---|
| Reaction time (min) | 20 | 20 | 60 | 60 | 60 | 60 | 60 |
| Conversion from cyclohexane (%) | 24.4 | 64.8 | 8.3 | 6.9 | 13.5 | 3.65 | 1.8 |
| Selectivity for adipic acid (%) | 56.1 | 71.6 | 36.4 | 14.9 | 61.0 | 4.79 | 0 |

*N-acetoxyphthalimide

TABLE 2

|  | Ex. 1 | Ex. 6 | Ex. 7 |
|---|---|---|---|
| Cyclohexane concentration (wt. %) | 65 | 65 | 65 |
| NHPI (mol %) | 0.2 | 0.05 | 0.025 |
| Co(acac)$_3$ (mol %) | 0.1 | 0.025 | 0.0125 |
| Co(OAc)$_2$ (mol %) | 0.1 | 0.025 | 0.0125 |
| Reaction temperature (° C.) | 110 | 110 | 110 |
| Reaction time (min) | 20 | 20 | 20 |
| Conversion from cyclohexane (%) | 24.4 | 21.7 | 20.5 |
| Selectivity for adipic acid (%) | 56.1 | 57.0 | 55.4 |

| Charged material composition | |
|---|---|
| Cyclohexane: | 45% by weight (2.939 mol) |
| Acetic acid: | 53.93% by weight |
| N-Hydroxysuccinimide: | 0.07% by weight |
| Cobalt (II) acetate tetrahydrate: | 1% by weight |

The inside of the reactor (autoclave) was pressurized to 3 MPa with nitrogen gas, and the temperature was raised while rotating the agitator at 500 rpm. At the time when the inside

TABLE 3

|  | Ex. 8 | Ex. 9 | Ex. 10 | Ex. 11 | Ex. 12 | Ex. 13 | Ex. 14 | Ex. 15 | Com. Ex. 2 | Com. Ex. 3 |
|---|---|---|---|---|---|---|---|---|---|---|
| Cyclohexane concentration (wt %) | 45 | 65 | 45 | 45 | 45 | 45 | 65 | 45 | 65 | 65 |
| NHPI (mol %) | 0.2 | 0.2 | 0.2 | 0.2 | 0.2 | 0.2 | 0.2 | 0.2 | — | 0.2 |
| Mn(acac)$_2$ (mol %) | — | — | 0.1 | — | — | — | 0.2 | — | 0.2 | — |
| Mn(acac)$_3$ (mol %) | — | — | 0.1 | — | — | — | — | — | — | — |
| Fe(lac)$_2$ (mol %) | — | — | — | 0.1 | — | — | — | — | — | — |
| Fe(acac)$_3$ (mol %) | — | — | — | 0.1 | — | — | — | — | — | — |
| Co(acac)$_3$ (mol %) | 0.01 | 0.2 | — | — | — | — | — | 0.1 | — | — |
| Co(OAc)$_2$ (mol %) | 0.01 | — | — | — | — | — | 0.02 | 0.1 | 0.02 | — |
| CuCl (mol %) | — | — | — | — | 0.1 | 1.0 | — | — | — | — |
| Cu(OAc)$_2$ (mol %) | — | — | — | — | 0.1 | 1.0 | — | — | — | — |
| Reaction temperature (° C.) | 110 | 110 | 110 | 110 | 110 | 110 | 110 | 100 | 110 | 110 |
| Reaction time (min) | 60 | 60 | 60 | 60 | 60 | 60 | 60 | 60 | 60 | 60 |
| Conversion from cyclohexane (%) | 17.5 | 13.8 | 38.9 | 14.3 | 13.0 | 36.6 | 14.7 | 8.8 | 0.11 | 0.23 |
| Selectivity for adipic acid (%) | 45.8 | 58.8 | 71.5 | 31.8 | 38.8 | 62.1 | 62.9 | 17.9 | 0 | 0 |
| Reaction solvent | acetic acid | acetic acid | acetic acid | acetic acid | acetic acid | acetic acid | acetic acid | acetonitrile | acetic acid | acetic acid |

TABLE 4

|  | Ex. 16 | Ex. 17 | Ex. 18 |
|---|---|---|---|
| Cyclododecane concentration (wt. %) | 65 | 40 | 40 |
| NHPI (mol %) | 0.2 | 0.2 | 0.4 |
| Mn(acac)$_2$ (mol %) | 0.2 | 0.2 | 0.04 |
| Co(OAc)$_2$ (mol %) | 0.02 | 0.02 | 0.4 |
| Reaction temperature (° C.) | 100 | 100 | 100 |
| Reaction time (hr) | 6 | 4 | 4 |
| Conversion from cyclododecane (%) | 20.6 | 26.5 | 16.1 |
| Selectivity for dodecanedioic acid (%) | 23.7 | 21.4 | 27.5 |

Example 20

A total of 550 g of a mixture having the following composition was charged into a 1-L autoclave with a titanium jacket having an agitator including three paddle blades and an agitating motor, an opening for charging an oxygen-containing gas, and another opening for extracting gaseous components.

temperature of the reactor reached 100° C., air supply at a flow rate of 100 L (normal conditions) per hour was started. Immediately after the beginning of air supply, a reaction began and the temperature was raised to some extent. While keeping the inner temperature of the reactor at 100° C., the reaction was continued for 120 minutes. The supplied gas was changed to nitrogen gas, and the reaction mixture was cooled. At the time when the temperature of the reaction mixture reached room temperature, the gas in the reactor was released, and the reaction mixture was extracted.

The reaction mixture had separated into two liquid-phase layers and was mixed with acetic acid in equal proportions to thereby yield a homogenous one layer, followed by analysis to find that a conversion from cyclohexane was 15.4% and a selectivity for adipic acid was 54.2% (0.245 mol). In addition, cyclohexanone (0.113 mol; selectivity: 25.0%), cyclohexanol (0.059 mol; selectivity: 13.1%), cyclohexyl acetate (0.009 mol; selectivity: 2.0%), glutaric acid (0.023 mol; selectivity: 5.1%), succinic acid (0.014 mol), and succinimide (0.0015 mol) were by-produced.

Example 21

The procedure of Example 20 was repeated, except that the composition of charged materials to the reactor was changed as follows.

| Charged material composition | |
|---|---|
| Cyclohexane: | 45% by weight (2.939 mol) |
| Acetic acid: | 53.90% by weight |
| N-Hydroxyphthalimide | 0.1% by weight |
| Cobalt (II) acetate tetrahydrate: | 1% by weight |

The reaction mixture had separated into two liquid-phase layers and was mixed with acetic acid in equal proportions to thereby yield a homogenous one layer, followed by analysis to find that a conversion from cyclohexane was 15.1% and a selectivity for adipic acid was 50.8% (0.226 mol). In addition, cyclohexanone (0.113 mol; selectivity: 25.4%), cyclohexanol (0.0589 mol; selectivity: 13.2%), cyclohexyl acetate (0.008 mol; selectivity: 1.8%), glutaric acid (0.023 mol; selectivity: 5.2%), succinic acid (0.009 mol; selectivity: 2.0%), phthalimide (0.0013 mol), and phthalic acid (0.0017 mol) were by-produced.

What is claimed is:

1. A process for producing a dicarboxylic acid by oxidative cleavage of a corresponding cycloalkane with oxygen, which comprises:

reacting in the presence of a catalyst a mixture comprising an imide compound and a metallic compound, the imide compound has a cyclic imide skeleton represented by following Formula (I):

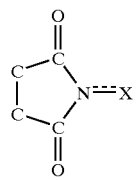

(I)

wherein X is an oxygen atom or an —OR group, and where R is a hydrogen atom or a hydroxyl-protecting group, under conditions of a reaction temperature of 80° C. or higher and a concentration of the cycloalkane of 21% by weight or more.

2. The process for producing a dicarboxylic acid according to claim 1, wherein the imide compound is a compound represented by following Formula (1):

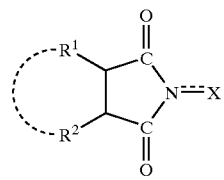

(1)

wherein $R^1$ and $R^2$ are the same or different and are each a hydrogen atom, a halogen atom, an alkyl group, an aryl group, a cycloalkyl group, a hydroxyl group, an alkoxy group, a carboxyl group, an alkoxycarbonyl group, or an acyl group, where $R^1$ and $R^2$ may be combined to form a double bond, an aromatic ring, or a non-aromatic ring; X is an oxygen atom or an —OR group, where R is a hydrogen atom or a hydroxyl-protecting group; and wherein one or two of an N-substituted cyclic imido group may be further formed on the $R^1$, $R^2$, or on the double bond, aromatic ring or non-aromatic ring formed by $R^1$ and $R^2$.

3. The process for producing a dicarboxylic acid according to claim 1, wherein the imide compound is N-hydroxysuccinimide which may have an alkyl group at the α-position and/or the β-position and whose hydroxyl group may be protected by a protecting group.

4. The process for producing a dicarboxylic acid according to claim 1, wherein the amount of the imide compound is from 0.000001 to 0.01 mole per mole of the cycloalkane.

5. The process for producing a dicarboxylic acid according to claim 1, wherein the metallic compound contains at least one metallic element selected from the group consisting of Groups 5, 6, 7, 8, 9, 10, and 11 of the Periodic Table.

6. The process for producing a dicarboxylic acid according to claim 1, wherein the metallic compound comprises a low-valence metallic compound and a high-valence metallic compound in combination, wherein when a metal has plural valences, the metallic compound having a lower valence is the low-valence metallic compound and the metallic compound having a higher valence is the high-valence metallic compound.

7. The process for producing a dicarboxylic acid according to claim 1, wherein the amount of the metallic compound is from 0.05 to 20 moles per mole of the imide compound.

8. The process for producing a dicarboxylic acid according to claim 1, further comprising using at least one solvent selected from protonic organic solvents and nitriles as a reaction solvent.

9. The process for producing a dicarboxylic acid according to claim 1, wherein the cycloalkane is a compound having a cycloalkane ring containing 5 to 15 members.

10. The process for producing a dicarboxylic acid according to claim 1, wherein the reaction temperature is from 80° C. to 200° C.

11. The process for producing a dicarboxylic acid according to claim 1, wherein the reaction temperature is from 80° C. to 150° C.

12. The process for producing a dicarboxylic acid according to claim 1, wherein the reaction temperature is from 90° C. to 140° C.

13. The process for producing a dicarboxylic acid according to claim 1, wherein the reacting is performed at a pressure of 0.5 to 20 MPa.

14. The process for producing a dicarboxylic acid according to claim 1, wherein the reacting is performed in the presence of oxygen.

* * * * *